United States Patent [19]

Takahashi et al.

[11] 4,428,868
[45] Jan. 31, 1984

[54] 5-METHYL-2-(2'-OXO-3'-BUTYL)PHENOL AND PERFUME COMPOSITIONS COMPRISING SAME

[75] Inventors: Katsuhiro Takahashi; Toshio Yoshida, both of Yokohama, Japan

[73] Assignee: Takasago Perfumery Co., Ltd., Tokyo, Japan

[21] Appl. No.: 349,908

[22] Filed: Feb. 18, 1982

[30] Foreign Application Priority Data

Feb. 20, 1981 [JP] Japan .................... 56-23872

[51] Int. Cl.³ .............. A61K 7/46; C07C 49/21
[52] U.S. Cl. .................... 252/522 R; 568/308
[58] Field of Search .................... 568/308; 252/522 R

[56] References Cited

FOREIGN PATENT DOCUMENTS 58906  9/1982  European Pat. Off. .

*Primary Examiner*—Anton H. Sutto
*Attorney, Agent, or Firm*—Oblon, Fisher, Spivak, McClelland & Maier

[57] ABSTRACT

The novel compound of 5-methyl-2-(2'-oxo-3'-butyl)phenol represented by the formula

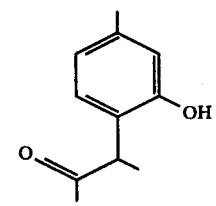

(I)

This compound emits a characteristic sweet fragrance and a perfume composition comprising this compound is also provided.

3 Claims, 1 Drawing Figure

5-METHYL-2-(2'-OXO-3'-BUTYL)PHENOL AND PERFUME COMPOSITIONS COMPRISING SAME

BACKGROUND OF THE INVENTION

Field of the Invention

This invention relates to a novel m-cresol derivative emitting specific sweet fragrance and also to perfume compositions comprising the same.

We have made a study on various cresol derivatives and found that a novel compound of 5-methyl-2-(2'-oxo-3'-butyl)phenol represented by the following formula

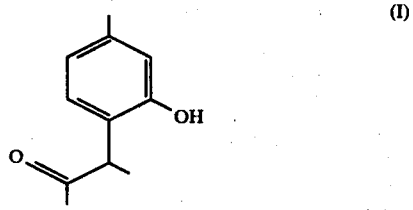

has excellent properties as a perfume substance. This novel compound can be synthesized with ease from starting m-cresol through a series of steps.

SUMMARY OF THE INVENTION

Accordingly, it is an object of the invention to provide a novel cresol derivative which is useful as an ingredient for perfume.

It is another object of the invention to provide a perfume composition comprising the cresol derivative of the just-mentioned type.

The above objects can be achieved, according to one aspect of the invention, by a compound of 5-methyl-2-(2'-oxo-3'-butyl)phenol represented by the formula

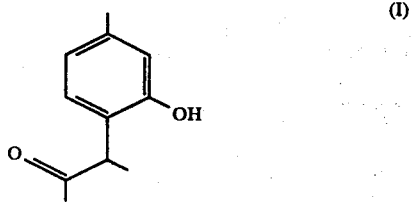

According to another aspect of the invention, there is provided a perfume composition which comprises an effective amount of the compound of the formula defined above.

BRIEF DESCRIPTION OF THE DRAWING

The sole FIGURE is the NMR spectrum for the compound of the invention obtained in Example 1.

DETAILED DESCRIPTION AND A PREFERRED EMBODIMENT OF THE INVENTION

Figure 1:
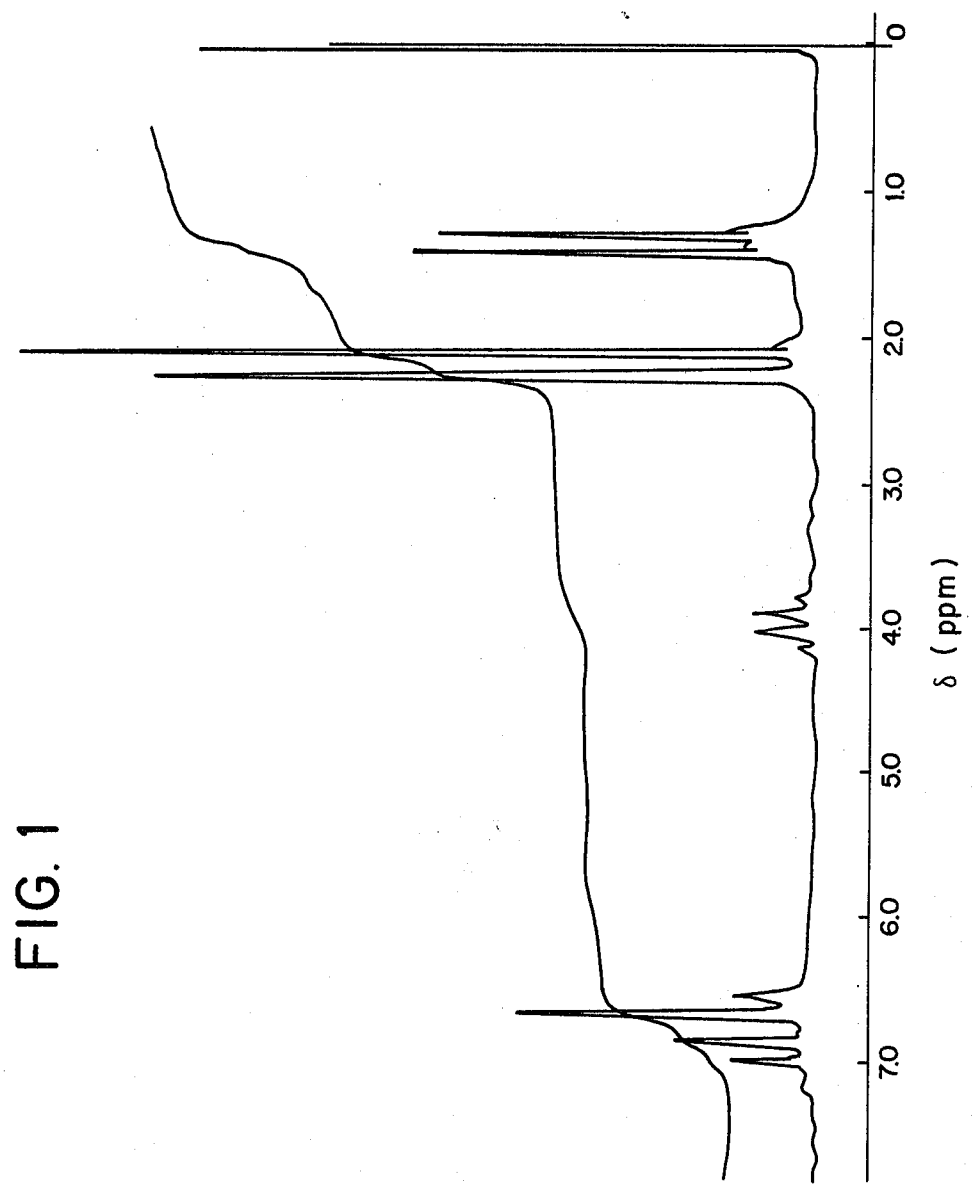

The compound of the formula defined above can be produced by a process which comprises reacting starting m-cresol with 1-chloro-2-butene (crotylchloride) or with 1-bromo-2-butene (crotylbromide) to form crotyl-3-methyl phenyl ether, subjecting the ether to the process if J. Borgulya et al described in Helv. Chim. Acta, 46, 2444 (1963), that is, the so-called Claisen rearrangement, thereby obtaining 2-(1'-buten-3'-yl)-5-methylphenol, isomerizing the same by the process of G. Ohloff et al described in Helv, Chim. Acta, 48, 1665 (1965) to form 2,(2'-buten-2'-yl)-5-methylphenol, and finally reacting it with an organic peracid such as peracetic acid or methachloroperbenzoic acid.

In practice, the above process is carried out, for example, as follows. At first, m-cresol and 1-chloro-2-butene (crotyl-chloride) or 1-bromo-2-butene (crotyl-bromide) are dissolved in anhydrous acetone, to which anhydrous potassium carbonate is added, and they are heated to 60° C. for reflux over three hours while stirring. After the completion of the stirring, water is added, followed by extraction with ether or the like. The ether phase, after being washed with an aqueous 10% solution of sodium hydroxide, is dried and then the ether removed through distillation. The concentrate is dissolved in diethyl aniline, heated to 180° C. and continuously agitated for about 16 hours. After the end of the reaction, the product is washed with 10% hydrochloric acid and further with water. Distillation under reduced pressure gives a fraction boiling at 77°–89° C./2mmHg. The fraction is added dropwise to the reaction product of ethylenediamine and metallic lithium at 110°–125 ° C. After the end of the addition, the reaction product is poured into ice water and extracted with ether or the like. The ether phase is washed with 10% hydrochloric acid, further washed with water and then dried. After distilling off the ether, the residue is distilled under a reduced pressure to obtain a fraction boiling at 70°–80° C./2mmHg. The fraction is dissolved in a solvent such as dichloromethane or carbon tetrachloride. Further, sodium carbonate is added and peracetic acid is added dropwise while cooling to 0°–5° C. After the end of the addition, the reaction is continued as it is for 30 minutes. After the end of the reaction, the product is treated in a conventional manner, distilled under a reduced pressure and purified to obtain 5-methyl-2-(2'-oxo-3'-butyl)phenol.

The compound obtained by the process referred to above is a white crystalline substance at room temperature, has a characteristic sweet perfume like that of fruit or molass and can be added for formulation into various perfume compositions. For instance, it can be formulated in about 0.1% upon preparation of synthetic essential oils such as peppermint, spearmint, lemon, orange or lime, so that it significantly contributes to the increase of the natural perfume and taste of these formulated products, thus exhibiting excellent effects. Furthermore, the present compound can be synthesized industrially with ease from those starting materials that can be available easily, and is thus very useful as the perfume ingredient. In a preferred aspect, the novel compound is added to any arbitrary perfume compositions in an amount of 1 to 2000 PPM.

This invention is described by way of Examples.

EXAMPLE 1

Into a 2 liters reaction flask equipped with a stirrer, a cooling tube and a thermometer, are charged 259 g (2.4 mol) of m-cresol, 229 g (2.53 mol) of 1-chloro-2-butene and 500 ml of anhydrous acetone, and they are heated while stirring, followed by addition of 349 g of anhydrous potassium carbonate and refluxing at 65° C. over 3 hours. After the completion of the reaction, 500 ml of water are added and then extracted with 500 ml of ethyl ether. The ethyl ether phase, after being washed with an aqueous 10% solution of sodium hydroxide, is dried over sodium sulfate. The ethyl ether is distilled off under a reduced pressure to obtain 350 g of crotyl-3-methyl phenyl ether (90% of the theoretical yield based on the m-cresol). Then, the crotyl 3-methyl phenyl ether is charged into a one liter reaction flask and, with addition of 500 ml of diethylaniline, heated to 180°–185° C. and stirred for 16 hours. After the completion of the stirring, the product is cooled to room temperature, washed with 500 ml of 10% hydrochloric acid and washed twice with 500 ml of water. The reaction product is found to contain 2-(1'-buten-3'-yl)-5-methylphenol (1) and 2-(1'-buten-3'-yl)-3-methylphenol (2):

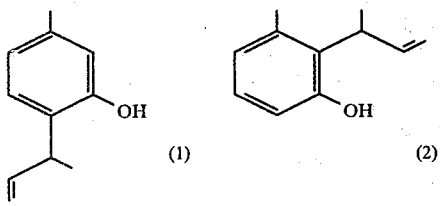

in 2:1 ratio as the result of instrumental analysis. The mixture is distilled under a reduced pressure to obtain 162 g of 2-(1'-buten-3'-yl)-5-methylphenol boiling at 77°–89° C./2mmHg (41.6% of the theoretical yield based on the crotyl-3-methylphenyl ether). Then, 162 g of 2-(1'-buten-3'-yl)-5-methylphenol are added dropwise to 187.5 g of ethylenediamine and 8.4 g of metallic lithium, which have previously been reacted under stirring, while keeping the reaction temperature to 110°–125° C. for about one hour. After the completion of the addition, the reaction product is poured into 500 ml of ice water and extracted with 500 ml of ethyl ether. The ether phase is washed with 300 ml of 10% hydrochloric acid, further washed twice with 300 ml of water and dried over sodium sulfate. Thereafter, the ether is distilled off to obtain a concentrated product. The concentrate is distilled under a reduced pressure to obtain 160 g of 2-(2'-buten-2'-yl)-5-methylphenol boiling at 70°–80° C./2mmHg (41.1% of the theoretical yield based on the crotyl-3-methylphenyl ether). 160 g of 2-(2'-buten-2'-yl)-5-methylphenol are dissolved in 320 ml of dichloromethane and, with further addition of 73.6 g of sodium carbonate, 226 g of 40% peracetic acid are dropped under stirring for 2 hours while keeping the temperature at 0°–5° C. After the end of the addition, stirring is continued for 30 minutes. After the end of the stirring, they are washed three times with 300 ml of an aqueous 20% sodium thiosulfate solution, washed twice with 300 ml water and dried over sodium sulfate, and the dichloromethane is removed through distillation. The concentrate thus obtained is distilled under a reduced pressure to obtain 115 g of 5-methyl-2-(2'-oxo-3'-butyl)phenol, 26.9% of the theoretical yield based on the crotyl-3-methyl phenyl ether) boiling at 110°–120° C./2mmHg. The present compound is obtained as white crystals after distillation and has the following properties.

m.p.: 67°~68.5° C.

M S (m/z): 178 (M+), 160, 136, 135, 117, 91

I R (cm$^{-1}$): 3375, 1700, 1425, 1290, 950, 820

N M R (δppm): 1.35 (d, 3H), 2.10 (s, 3H), 2.26 (s, 3H), 3.95 (q, 1H), 6.65 (d, 1H), 6.68 (s, 1H), 6.94 (d, 1H)

The compound (1) shows the NMR spectrum as shown in FIG. 1.

EXAMPLE 2

A formulated perfume composition having peppermintlike flavour was prepared according to the following formulation:

| Peppermint | (parts by weight) |
|---|---|
| α-pinene | 9 |
| β-pinene | 12 |
| limonene | 16 |
| p-thymene | 3 |
| cariophyllene | 5 |
| 3-octanol | 3 |
| linalool | 4 |
| menthol | 420 |
| neomenthol | 30 |
| isomenthol | 7 |
| 4-terpinenol | 33 |
| α-terpineol | 20 |
| 2-methyl isovalerate | 2 |
| isoamyl isovalerate | 1 |
| methyl acetate | 37 |
| isovaleraldehyde | 2 |
| cis-jasmone | 2 |
| menthone | 265 |
| isomenthone | 36 |
| piperitone | 5 |
| pulegone | 1 |
| menthofuran | 17 |
| 1,8-cineole | 68 |
| 1-octen-3-ol | 2 |
| | 1,000 |

To 100 g of the formulated perfume, were added 0.001 g (corresponding to 10 ppm) of the compound (1) obtained in Example 1. As the result of the evaluation determined by 10 expert panels, all of the panels recognized that natural flavour was significantly improved for the product with addition of the compound (1) as compared with the product with no such addition.

EXAMPLE 3

A formulated perfume having orange-like flavour was prepared according to the following formulation:

| Orange | (parts by weight) |
|---|---|
| α-pinene | 4 |
| β-pinene | 3 |
| myrcene | 10 |
| limonene | 921 |
| γ-terpinene | 3 |
| p-thymene | 1 |
| terpinoline | 2 |
| octanal | 2 |
| cis-3-hexenal | 0.5 |
| nonanal | 1 |
| citronellal | 0.5 |
| decanal | 3 |
| linalool | 4 |
| linalyl acetate | 0.5 |
| octanol | 0.4 |
| 4-terpinenol | 0.2 |
| α-terpineol | 9 |
| citral | 20 |
| neryl acetate | 3 |
| geranyl acetate | 3 |
| nerol | 0.5 |
| geraniol | 1 |
| α-farnesene | 5 |
| perillaldehyde | 0.2 |
| limonen alcohol | 0.2 |
| nootkatone | 1 |
| | 1,000 |

To 100 g of the formulated perfume, were added 0.001 g (corresponding to 10 ppm) of the compound (1) obtained in Example 1. As the result of the estimation determined by 10 expert panels, all of the panels recognized that natural flavour was significantly improved for the product with addition of the compound (1) as compared with the product with no such addition.

What is claimed is:

1. 5-methyl-2-(2'-oxo-3'-butyl)phenol represented by the formula

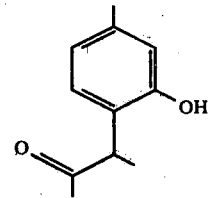

2. A perfume composition comprising an effective amount of 5-methyl-2-(2'-oxo-3'-butyl)phenol represented by the formula (I)

3. A perfume composition according to claim 2, wherein the phenol compound is used in an amount of 1 to 2000 PPM.

* * * * *